United States Patent [19]

Cotter

[11] Patent Number: 4,850,964
[45] Date of Patent: Jul. 25, 1989

[54] BLOOD COLLECTION DEVICE

[76] Inventor: Robert F. Cotter, 73 Broad Reach St., N. Weymouth, Mass. 02191

[21] Appl. No.: 107,938

[22] Filed: Oct. 13, 1987

[51] Int. Cl.$^4$ ............................................. A61M 37/00
[52] U.S. Cl. ........................................ 604/4; 604/319; 604/322; 604/406
[58] Field of Search ................. 604/4, 5, 35, 48, 49, 604/51, 317, 318, 319, 322, 403, 406, 902; 128/DIG. 3, 760

[56] References Cited

U.S. PATENT DOCUMENTS

| | | | |
|---|---|---|---|
| 2,848,995 | 8/1958 | Ryan | 604/406 |
| 3,492,991 | 2/1970 | Dyer, Jr. | 604/5 |
| 3,507,395 | 4/1970 | Bentley | 604/4 |
| 3,891,416 | 6/1975 | Leonard et al. | 604/317 |
| 4,033,724 | 7/1977 | Tamiya | 128/DIG. 3 |
| 4,047,526 | 9/1977 | Reynolds et al. | 604/4 |
| 4,188,360 | 2/1980 | Kurata | 128/DIG. 3 |
| 4,228,125 | 10/1980 | Lobdell et al. | 128/DIG. 3 |
| 4,261,951 | 4/1981 | Milev | 128/DIG. 3 |
| 4,443,220 | 4/1984 | Hauer et al. | 604/4 |

FOREIGN PATENT DOCUMENTS 2101892  1/1983  United Kingdom .................. 604/4

*Primary Examiner*—C. Fred Rosenbaum
*Assistant Examiner*—Mario Costantino
*Attorney, Agent, or Firm*—Donald Brown

[57] ABSTRACT

Blood collection system using a container having an inlet tube inside it and having a filter material coupled to the tube inside the container to collect debris contained within blood being fed into the container.

4 Claims, 1 Drawing Sheet

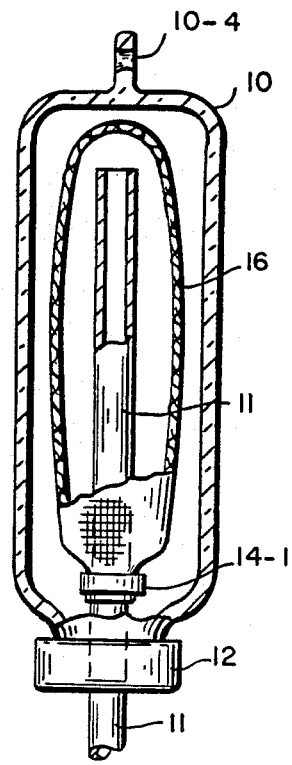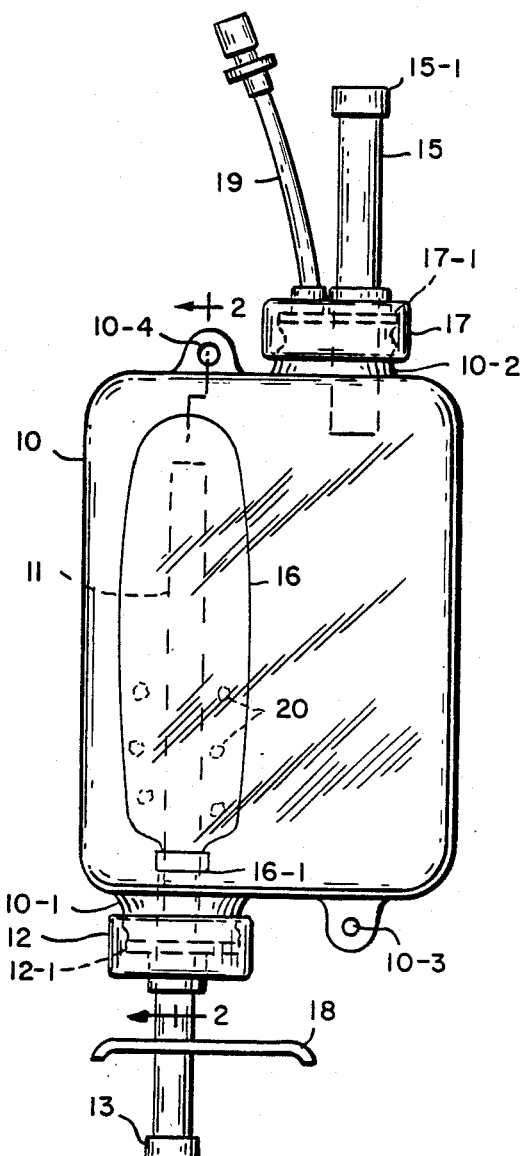
FIG. 2
FIG. 1

BLOOD COLLECTION DEVICE

BACKGROUND OF THE DISCLOSURE

Blood collection and resue thereof has become widely practiced during surgical operations. In some cases the blood is reinfused after collection in a bag system and in other instances, the blood is collected in a machine which cleans it prior to reinfusion.

A type of bag system in use in cases where direct reinfusion without machine cleaning is presently sold by Solco Basle Inc. of Rockland, Mass. under the trademark SOLCOTRANS. The SOLCOTRANS brand bag system includes a flexible bag in a rigid bottle which is adapted to operate to collect in and then reinfuse blood from the flexible bag and uses an aspirator handle with a filter in the handle or an external filter arrangement coupled to an aspirator handle with the filter then coupled by a tube to the bag.

It is desirable in orthopedic (bone) surgery to collect the blood from the wound and separate the blood from the bone chips prior to machine cleaning. While the Soloctrans brand bag system is acceptable for use in these circumstances, i.e., for use in conjunction with machine cleaning, it has now been determined herein that for machine cleaning applications a more simplied blood collection system and thus a less expensive system could be used. This application discloses such a system.

To show the state of the art, reference should be had to U.S. Pat. No. 4,573,992 and the patents cited therein.

BRIEF DESCRIPTION OF THE DISCLOSURE

The present invention discloses a simple and inexpensive blood collection device which is particularly suitable for the collection of blood in e.g., bone surgery which is then to be machine cleaned prior to reinfusion.

The device comprises a container having an elongated inlet tube positioned in part therein through which blood is collected and a filter material surrounding the outlet of the tube portion in the container and preferably coupled about the tube preferably a sufficient distance e.g., at least halfway down the length of the tube positioned in the container to provide a sufficient collection area for the collection of debris e.g., bone chips collected from the wound and an outlet tube coupled to the container to withdraw blood free of bone chips from the container.

BRIEF DESCRIPTION OF THE DRAWINGS

FIG. 1 is a side view of the device of the disclosure showing the collection of blood from a mammel (human) whose hip is undergoing surgery, and FIG. 2 is a sectional view taken along line 2—2 of FIGS. 1.

DETAILED DESCRIPTION OF THE DISCLOSURE

Reference should now be had to FIGS. 1 and 2 for a description of the invention.

At 10, there is shown a container e.g., of plastic such as polyethylene, PVC etc., and is preferably rigid i.e., it substantially holds its shape rather than being collapsable. The container 10 has threaded necks 10-1 and 10-2 and to which is applied sealing caps 12 and 17 respectively. The sealing cap 12 is provided with a sealing plastic washer 12-1 which is forced by the cap 12 against the neck 12-1. The tube 11 is supported by the washer 12-1 and has a tube 11 (e.g., of PVC) for providing blood into the interior of the container 10. The tube 11 preferably extends more than halfway, as shown, into the container 10. The tube 11 at its other end (which is outside the container 10) is coupled to a connector 13 and then to a tube 14 to collect blood from a human 30 undergoing orthopedic surgery e.g., a hip replacement. A conventional slotted clip is shown at 18 for closing off tube 11 if desired. As shown in FIGS. 1 and 2, there is provided a filter material 16 formed about the tube 11 and sealed at 16-1 by a conventional plastic adhesive material e.g, Locktite brand joining the filter to the tube and a plastic adhesive tape e.g., Teflon brand is positioned thereabout to secure the connection of the filter material about the tube.

The filter material may be a 260 mesh filter material and may be a mesh product such as made by Dupont. The filter material is of sufficient area so that it may collect debris 20 e.g., bone chips between its interior and the tube 11 outer side wall without effecting the passage of blood into the container and at the same time collection of debris takes place. The filter permits blood to flow through it into the interior of the container portion beyond the filter. At 10-3 and 10-4 there are provided hooks to hold the bag. The hooks as well as the openings 10-1 and 10-2 are preferably provided in the opposite end wall portions as shown in the drawing.

At 15, there is provided a tube to withdraw blood from the container 10. A cap 15-1 is provided to close the tube. The tube 15 is held within a sealing washer gasket 17-1 which is forced over the top neck of the container opening as shown. A second tube 19 with a vacuum closure may also be provided and which is supported by the gasket 17-1 to provide suction to withdraw blood or gas under pressure to force blood from the container 10.

In use, the tube 14 is placed in position to pick up blood in the portion of the patient being operated on and stored in the container 10 after passing through the mesh filter 16. Bone particles 20 are collected as shown in FIG. 1 from the surgical incision. Thereafter, clip 18 closed off and the blood is permitted to flow from the container through the tube 15.

I claim:

1. A system for collecting blood and then delivery of same comprising a plastic container which holds its shape and has two opposed ends spaced apart from each other a predetermined distance, said container defining a first opening in one end and a second opening in the other end, a tube having an open end for delivering blood into said container and extending through said first opening, said open end of said tube positioned away from the inner surface of the container, said tube having a length thereof extending a distance in said container towards said second opening more than halfway the distance between said first and second openings, a mesh filter material inside said container positioned about said tube length and coupled to said tube along its length at a distance more than half the length of the tube from the open end of the tube, said filter surrounding at least the open end of the tube, said filter material being of sufficient area and of a mesh material to permit blood to flow from said tube into said container and to collect solid debris carried with said blood and store same between said mesh inside said container and said length of tube from the point where said mesh is coupled to said tube, means coupled to said first end for supporting the tube in said first opening, and a tube coupled to said second opening to permit withdrawal of said blood from said container free from collected debris.

2. The system according to claim 1, in which there is provided a third tube coupled to the container and opening into said container for providing a vacuum to draw blood into said container and to provide gas under pressure to force blood from said container through said second tube.

3. A blood collection and readministration system compressing a container having four sides and first and second ends positioned apart a predetermined distance, said first end defining a first opening and said second end defining a second opening, a length of tube having an open end positioned in said first opening and extending a distance in said container towards said second opening more than half the distance between said first and second ends, a mesh filter positioned about and surrounding at least the open end of the tube and coupled about the tube inside said container at a distance more than three quarters the length of the tube from the open end so that debris can be collected between said tube and mesh filter, means coupled first about said first opening for supporting said tube in said container, and a second means coupled about said second opening for withdrawing blood from said container, said tube open end being spaced away from the interior side walls so that the mesh can surround the tube.

4. The system of claim 3 in which said second means includes a tube with an open end which extends into the container towards said first opening.

* * * * *